US006245363B1

(12) United States Patent
Myers et al.

(10) Patent No.: US 6,245,363 B1
(45) Date of Patent: Jun. 12, 2001

(54) METHODS OF TREATING PLANT MATERIALS WITH HYDROLYTIC ENZYMES ISOLATED FROM HUMICOLA SPECIES

(75) Inventors: Stephen John Myers, Ashford; Peter S.J. Cheetham, Turnbridge Wells; Nigel E. Banister, London, all of (GB)

(73) Assignee: Zylepsis Limited, Ashford (GB)

( * ) Notice: Subject to any disclaimer, the term of this patent is extended or adjusted under 35 U.S.C. 154(b) by 0 days.

(21) Appl. No.: 08/973,948

(22) PCT Filed: Jun. 7, 1995

(86) PCT No.: PCT/GB96/01345

§ 371 Date: Mar. 31, 1998

§ 102(e) Date: Mar. 31, 1998

(87) PCT Pub. No.: WO96/39859

PCT Pub. Date: Dec. 19, 1996

(30) Foreign Application Priority Data

Jun. 7, 1995 (WO) .................................. PCT/GB95/01324
Nov. 29, 1995 (GB) .................................................. 9524353

(51) Int. Cl.$^7$ ........................................................ A23K 1/14
(52) U.S. Cl. ................. 426/2; 426/53; 426/615; 426/629; 426/623; 426/630; 426/635; 426/807; 426/132
(58) Field of Search ................. 426/2, 615, 629, 426/630, 623, 635, 807, 53; 435/132

(56) References Cited

U.S. PATENT DOCUMENTS

| 4,038,481 | 7/1977 | Antrim et al. ........................ 536/56 |
| 4,158,656 | 6/1979 | Jones et al. ....................... 260/123.5 |
| 4,426,448 | 1/1984 | Okamura et al. ................... 435/146 |

FOREIGN PATENT DOCUMENTS 0 503 650 A2    9/1992  (EP) .

OTHER PUBLICATIONS

Dabrowski, K. and Sosulski, F., Quantification of free and hydrolyzable phenolic acids in seeds by capillary gas–liquid chromatography; J. Agrig. Food. Chem., pp. 123–127, vol. 32, 1984.

Salomonsson et al., "Quantitative determination by glc of phenolic acids as ethyl derivatives in cereal straws"; J. Agric. Food. Chem., pp. 830–835, vol. 26, no. 4, 1978.

Lanzani et al., "Removal of chlorogenic acid from sunflower seeds"; Actes Congf. Mond.—Soc. Int. Etude Corps Gras, 13th (1976), pp. 7–13, vol. 9, Paris.

Dominguez et al., "Aqueous processing of sunflower kernels with enzymatic technology"; Food Chemistry, pp. 427–434, vol. 53, no. 4, 1995.

MiCard et al., "Studies on enzymic release of ferulic acid from sugar–beet pulp"; Food Science and Technology, pp. 59–66, vol. 27, no. 1, 1994.

Castanares et al., "Purification and properties of a feruloyl/p–coumaroyl pinophilum"; Enzyme and Microbial Technology, pp. 875–884, vol. 14, no. 11, 1992.

Faulds, C. and Williamson, G., "Release of ferulic acid from wheat bran by a ferulic acid esterase (FAE–III) from aspergillus niger"; Applied Microbiology and Biotechnology, pp. 1082–1087, vol. 43, no. 6, 1995.

Varoquaux et al., "Partial characterization of hydroxycinnamoylquinate esterase from aspergillus niger"; Food Science and Technology, pp. 39–41, vol. 15, no. 1, 1982.

Primary Examiner—Chhaya D. Sayala
(74) Attorney, Agent, or Firm—Bromberg & Sunstein LLP

(57) ABSTRACT

The invention relates to methods for treating plant material such as sunflower seed meal with water and a hydrolytic enzyme in an aqueous environment to increase its nutritional value and to enzymatic methods for converting plant derived material into useful products.

24 Claims, No Drawings

METHODS OF TREATING PLANT MATERIALS WITH HYDROLYTIC ENZYMES ISOLATED FROM HUMICOLA SPECIES

The invention relates to methods for making useful products from precursors such as plant materials. The invention also relates to methods for converting said products into still further useful derivatives.

Large amounts of plant material are produced as a by-product of various manufacturing processes in the form of a pulp. For example, sunflower seed meal is produced as a by-product of sunflower oil manufacture. Sunflower seed meal has a high protein content (approximately 40%) which comprises significant amounts of nutritionally important amino acids. Thus it has potential as a human food or an animal feed. Until now, such plant material has received very little attention as a resource. Some plant material is used for animal feed, but its nutritional value is lowered by the presence of endogenous phenolic compounds, principally chlorogenic acid, an ester of caffeic acid and quinic acid. The phenolic compounds reduce the nutritional value of the plant material by binding to proteins, especially to essential amino acids such as lysine. Phenolic compounds are also known to cause discolouration of feed materials and extracted proteins [Smith and Johnsen, *Cereal Chem.*, 1948, 25, 339]. Removal of these phenolics will give a more acceptable foodstuff material. Attempts have been made to remove the phenolic compounds by solvent extraction, but in general these have failed principally because chlorogenic acid is relatively insoluble in organic solvents, and aqueous extraction procedures tend to remove both the chlorogenic acid and the nutritious protein from the plant material. (See Tranchino et al, Qual. Plant Plant Foods Hum. Nutr., 1983, 32, 305 for further information.) Extraction into organic solvents makes the process logistically inconvenient because of the necessity for sequential extractions (see Sripad et al., J. Biosci., 1982, 4, 145). Clearly, it would be desirable for the plant material to be put to better use According to the invention there is provided a method of treating plant material to increase its nutritional value comprising exposing it to a hydrolytic enzyme in an aqueous environment and removing phenolic compounds produced by hydrolysis using solvent extraction. Some suitable solvents are listed in Table 2.

The term plant material as used herein includes material such as the meal or pulp produced by mechanical processing of plants. The plant material typically comprises the residue or meal produced by mechanical processing of plant material or the residues remaining after the extraction of seed oils eg. sunflower seeds, rape seed, olives, potatoes, cereal grains, such as wheat or corn, coffee, soya bean, tobacco, grapes, sugar beet and such like.

By removing products of hydrolysis, such as caffeic acid produced by hydrolysis of chlorogenic acid as described, for example, in Example 1, the nutritional value of the remaining plant material is increased considerably. In the case of plant material in the form of processed rape seed, the method of the invention can be used to remove the excessively bitter taste caused by sinapine, an ester of sinapic acid and choline.

Thus the phrase "increase the nutritional value" used herein embraces improving the palatability of the plant material and, by removing discolouring phenolic compounds, the suitability/acceptability of the treated plant material as a food for humans or animals.

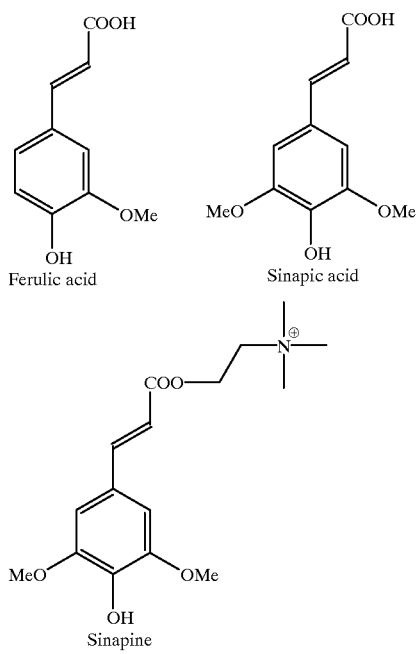

Ferulic acid    Sinapic acid

Sinapine

Whilst the methods of the invention can be used to improve the nutritional value of plant and plant-derived materials as food, the extracted products of hydrolysis such as caffeic acid, quinic acid, sinapic acid, choline, coumaric acid and ferulic acid are also valuable.

In a further aspect the invention provides a method of preparing a phenolic compound comprising treating a plant material by exposing it to a hydrolytic enzyme in an aqueous environment and removing the phenolic compound.

Preferably, the phenolic products are removed by solvent extraction.

Preferred hydrolytic enzymes for use in the methods of the invention are those which exhibit activity on an ester bond, hydrolysing the carbon oxygen bond to produce acid and alcohol moieties. These are the enzymes classified in the Enzyme Classification recommendations as E.C. 3.1. and subgroups thereof.

Preferably the hydrolytic enzyme does not exhibit a substantial proteolytic activity as such activity may reduce the nutritional value of the protein component of the treated plant material. Conveniently, the enzyme is isolated from Humicola, Bacillus and Aspergillus species or is isolated from porcine liver. Suitable enzymes include those listed in Table 1.

Preferred enzymes for use in the methods of the invention can be isolated by the selection procedure detailed in Example 10. This procedure involves screening candidate enzyme preparations for chlorogenic acid hydrolysis activity and the absence of a substantial proteolytic activity against bovine serum albumin. It will be appreciated that similar selection procedures can be used for other phenolic compounds of interest and other proteins could be employed in the optional proteolytic activity selection step.

The above screening methods form further aspects of the invention.

The enzyme preparation marketed by the Enzyme Process Division of Novo Nordisk, Denmark under the trademark Celluzyme® is particularly preferred for use in the methods of the invention. Celluzyme® is a cellulolytic enzyme preparation produced by submerged fermentation of the fungus *Hunicola insolens*. The enzyme complex is used in the laundering of cotton fabrics or mixed fabrics containing cotton.

Celluzyme is listed on relevant inventories of chemicals which are approved for use in cosmetics and foodstuffs, eg. EINECS (European Inventory of Existing Chemical Substances) and TSCA (Toxic Substances Control Act). Celluzyme is classified in Chemical Abstract Service as "Cellulase" (CAS No. 9012-54-8). The corresponding Enzyme Classification number (International Union of Biochemistry) is E.C. 3.2.1.4.

Another Novo Nordisk enzyme preparation useful in the methods of the invention is Bio-Feed™ Plus, a carbohydrase preparation produced by submerged fermentation of *Humicola insolens*. The enzyme hydrolyzes arabano-xylans and β-glucans into oligosaccharides and some mono-, di-and trisaccharides. Bio-Feed Plus contains other carbohydrase activities, including cellobiase, hemi-cellulase and cellulase.

A further enzyme preparation useful in the methods of the invention is sold by Biocatalysts Limited of Pontypridd, Wales, under the tradename Pectinase 162. Pectinase 162 is a wide activity spectrum pectinase derived from the Aspergillus species. The pectinase is effective on both soluble and insoluble pectins.

Advantageously, the plant material is derived from sunflower, rape, cereals including wheat, corn, potato and rice, or combinations thereof. However, skilled persons will appreciate that a variety of material from other plants can be used in the methods of the invention including material from tomatoes, olives, sugar beet or other available plants.

Preferably the method of the invention further comprises precipitating and isolating protein from the treated plant material.

Preferably the methods of the invention further comprise the step of administering the treated plant material or protein to a human or animal.

In a second aspect, invention provides a food comprising treated plant material or protein obtainable by the method of the invention. The food may be for human consumption or may be in the form of an animal feed.

The invention also relates to the use of the treated plant material or protein in a method of making a food product for human or animal consumption.

In a third aspect, the invention provides a method of converting sinapine to sinapic acid and choline comprising hydrolysing the sinapine enzymatically.

In a fourth aspect the invention provides a method of making sinapic acid and choline comprising the method of the third aspect and the further step of removing the products of hydrolysis.

In a fifth aspect the invention provides a method of producing ferulic acid comprising treating plant material by exposing it to a hydrolytic enzyme in an aqueous environment and removing the ferulic acid produced. Although plant material containing ferulic acid precursors is widespread throughout the plant kingdom, the plant is preferably wheat, or rice.

In a sixth aspect the invention provides a method of making caffeic acid and/or quinic acid by treating plant material containing chlorogenic acid by exposing it to a hydrolytic enzyme in an aqueous environment and removing, for example by solvent extraction, the products of hydrolysis.

Chlorogenic acid is a commonly available compound of the formula:

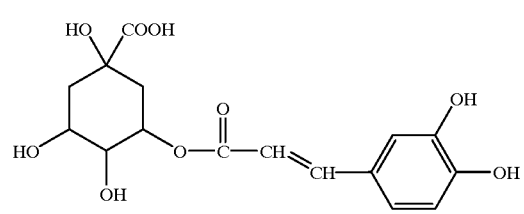

Caffeic acid is a molecule of the formula:

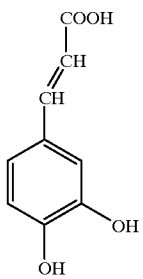

This molecule is known per se but is only of use as a research chemical. It is a natural molecule found in plants such as coffee. It is extremely difficult and expensive to produce and is available only in very small quantities. At present, the method of production of caffeic acid is by solvent extraction from plant tissue and column chromatography.

The present invention provides a novel inexpensive method for producing caffeic acid and derivatives thereof.

An advantage of the methods of the invention is that they do not require large liquid volumes and they allow direct enzyme treatment of the plant material. Preferably, the ratio of plant material to water is from 1:10 or less dilute (ie. is ($\leq$1):10) and more preferably from 1:5 to 1:2, especially 1:3. Smaller liquid volumes are advantageous because a smaller total volume of solvent has to be extracted following the reaction to remove the products of hydrolysis. Furthermore, less water has to be removed in drying the residual treated plant material. Thus, the methods of the invention can be carried out on thick slurries of plant material containing a minimum amount of water so that the total volume of material that has to be processed is reduced to a minimum.

The protein component of the treated plant material can be extracted by adjusting the pH of the plant material solution to an alkaline pH so that the protein is solubilized The remaining solid material is removed, for example by filtration, and the protein is precipitated from the solution by reducing the pH to an acidic pH. The precipitated protein can be collected, for example by filtration, and dried. Suitable methods are described by Niazi, A. H. K. et al, Sci. Int.

(Lahore), 1994, 6, 249–250 and Trachino, L. et al, Qual. Plant Plant Foods Hum Nutr, 1983, 32, 305–334. The protein produced can be used in a variety of applications such as food for humans or as animal feed.

The methods of the invention allow waste plant material to be converted into products which have considerable commercial value.

TABLE 1

Enzymes capable of hydrolysing chlorogenic acid

| Enzymes | Source | Source organism |
|---|---|---|
| Biofeed Plus | N | Humicola insolens |
| Biofeed Beta | N | Bacillus subtilis Humicola insolens |
| Fungamyl Super 5000 MG | N | |
| Celluzyme | N | Humicola insolens |
| Energex | N | Aspergillus niger |
| Fungamyl L | N | Aspergillus oryzae |
| Viscozyme L | N | Aspergillus niger |
| Macer 8(O) | B | Aspergillus sp. |
| Macer 8(W) | B | Aspergillus sp. |
| Macer 8(R) | B | Aspergillus sp. |
| Macer 8(FJ) | B | Aspergillus sp. |
| Pectinase 162 | B | Aspergillus sp. |
| Depol 40 | B | — |
| Depol 165 | B | — |
| Esterase (E3128) | S | Porcine liver |
| Protease (P4755) | S | Aspergillus oryzae |
| Pectolase | G | Aspergillus niger |

Key:
N = Novo Nordisk
B = Biocatalysts Ltd
S = Sigma
G = Grinstead

TABLE 2

List of solvents suitable for extraction of caffeic acid from plant material such as treated sunflower meal

| Solvent(s) | Vol (ml) | Mass of meal | Mass of extract | Amount of caffeic acid in extract (%) |
|---|---|---|---|---|
| Ethyl acetate | 300 | 50 | 0.52 | 21.1 |
| Isopropyl alcohol (IPA) | 300 | 50 | 8.73 | 1.89 |
| IPA/Water (1:1) | 300 | 50 | 9.5 | 2.23 |
| IPA/Water (4:1) | 300 | 50 | 11.52 | 1.08 |
| n-Butanol | 300 | 50 | 1.73 | 13.1 |
| Ethanol | 300 | 50 | 9.29 | 1.5 |
| Hexanol | 300 | 50 | 1.04 | 4.13 |
| Chloroform/methanol/water (25:25:1) | 100 | 5 | 0.94 | 4 |

Preferred embodiments of the invention will now be described by way of example with reference to the following examples EXAMPLE 1
Extraction and hydrolysis of chlorogenic acid in sunflower meal to caffeic acid by Celluzyme Pelleted sunflower meal (50 g) was added to an aqueous solution (175 ml) containing Celluzyme (2 g; Novo Nordisk). The reaction was mixed manually and heated via water bath (45° C.). The pH of the reaction mixture was monitored using a pH meter and held at pH 7.0 by the addition of aqueous sodium hydroxide (1.0 M). The hydrolysis of chlorogenic acid was monitored by High Performance Liquid Chromatography (HPLC) analysis and when completed after 5 hours incubation the reaction was terminated by addition of concentrated hydrochloric acid (0.7 ml). The reaction mixture was extracted with ethyl acetate (200 ml+100 ml) which was separated, pooled, dried over sodium sulphate and dried with heating in vacuo.

Yield of extract=0.52 g (caffeic acid content 21%)
Yield of treated sunflower meal (oven dried)=40.84 g.
HPLC assay conditions for chlorogenic acid and caffeic acid Samples for assay were directly injected onto a $C_{18}$ reverse phase chromatography column on a Waters high pressure liquid chromatography rig. The carrier phase was a 20:80 v/v mixture of acetonitrile:water containing 1% v/v acetic acid eluting at 2 ml/min. The substrate and products of the reaction were detected by a UV detector monitoring at 320 nm.

EXAMPLE 2
Effect of sunflower meal to water ratio on hydrolysis of chlorogenic acid from sunflower meal by Celluzyme Data for the effect of sunflower meal (SFM) to water ratio is summarised in the following table. This demonstrates that the overall yield of caffeic acid from the meal is comparable for the 1:10 and 1:3 ratios although the latter resulted in a larger mass of extract. The lower ratio is advantageous in that the reaction has a smaller volume per mass of meal, a smaller volume has to be extracted to remove the caffeic acid and less water has to be removed in drying the meal.

| Ratio (SFM:water) | Yield of extract from SFM (%) | Caffeic acid in extract (%) | Caffeic acid yield from SFM (%) |
|---|---|---|---|
| 1:10 | 2.2 | 46 | 1.12 |
| 1:5 | 2.2 | 34 | 0.74 |
| 1:3 | 3.2 | 37 | 1.18 |

EXAMPLE 3
Effect of pH and temperature on activity of Celuzyme towards chlorogegnic acid producing caffeic acid Rate of hydrolysis of chorogenic acid demonstrated that the optimum pH of Celluzyme was pH 8. Optimum temperature is in the range 45–55° C.; at 65° C. the enzyme was found to be unstable. pH 7 was used for hydrolysis reactions as the rate of oxidation of chlorogenic acid and caffeic acid was lower than at pH 8.

Rate of chlorogenic acid hydrolysis:
pH 4<5<6<7<8>9
Temp. 55° C.>45° C.

EXAMPLE 4
Enzymatic production of ferulic acid from wheat germ
Method

Wheat germ (10 g) was added to water (100 ml, pH 7.0) in a water jacketed reaction cell (45° C.) and stirred using a magnetic follower. A pH stat was used to hold the reaction at pH 7.0 by dosing aqueous sodium hydroxide (1.0 M). The amount of ferulic acid extracted in one hour was determined by HPLC and Celluzyme (200 mg; Novo Nordisk) added. After 8000 sec. the amount of ferulic acid extracted was again measured by HPLC: Area of peak=$1.11 \times 10^8$ (~33 µg/ml), retention time (RT)=5.13 min.

An identical control reaction without addition of Celluzyme was performed. After 8000 sec. the amount of ferulic acid extracted was again measured by HPLC: Area of peak=$3.31\times10^7$(~2 µg/ml), RT=5.06 min.

HPLC conditions: $C_{18}$ reverse phase column, 2 ml/min flow rate, 290 nm detector absorbance, acetonitrile/water (20:80)+1% acetic acid mobile phase. Ferulic acid retention time was comparable to standards for both the enzymatic and control reactions.

EXAMPLE 5
Ability of Pectinase 162L to hydrolyse ch orogenic acid to caffeic acid in an extract of sunflower meal Method Sunflower meal extract was prepared by incubating sunflower meal (10 g) with water (100 ml) at 45° C. and pH 8.0 for 20 min. To 20 ml of this extract (filtered and adjusted to pH 7.0 using hydrochloric acid (1.0 M)) was added Pectinase 162 L (400 µl; Biocatalysts Ltd.) in a water jacketed reaction vessel stirred via a magnetic follower. A pH Stat was used to hold the reaction at pH 7.0 by dosing aqueous sodium hydroxide (1.0M). The hydrolysis of chlorogenic acid to caffeic acid was monitored by HPLC analysis at t=0, 0.5, 1 and 2 hr.

| Time (hr) | Chlorogenic acid (mg/ml) | Caffeic acid (mg/ml) |
|---|---|---|
| 0 | 1.49 | 0.02 |
| 0.5 | 1.1 | 0.18 |
| 1 | 1.02 | 0.2 |
| 2 | 0.81 | 0.23 |

EXAMPLE 6
Ability of Biofeed Plus CT to hydrolyse chlorogenic acid to caffeic acid in an extract of sunflower meal Method Sunflower meal extract was prepared by incubating sunflower meal (10 g) with water (100 ml) at 45° C. and pH 8.0 for 20 min. To 5 ml of this extract (filtered and adjusted to pH 7.0 using hydrochloric acid (1.0M)) was added Biofeed Plus CT (10 mg; Novo Nordisk). The solution was incubated at 45° C. and shaken at 200 rpm. The hydrolysis of chlorogenic acid to caffeic acid was monitored by HPLC analysis at t=0, 1 and 4 hr.

| Time (hr) | Chlorogenic acid (mg/ml) | Caffeic acid (mg/ml) |
|---|---|---|
| 0 | 1.29 | 0.01 |
| 1 | 0.68 | 0.55 |
| 4 | 0.19 | 0.66 |

EXAMPLE 7
Hydrolysis of chlorogenic acid in sunflower meal to caffeic acid by Viscozyme Method Sunflower meal (10 g) was incubated with water (100 ml) at 45° C. and pH 8.0 for 60 min. The pH was monitored and adjusted to pH 8.0 during this period by addition of sodium hydroxide solution (1.0 M). The solution (20 ml) containing sunflower meal solids was decanted into a clean flask and Viscozyme (1.4 ml; Novo Nordisk) added. A control reaction without the addition of Viscozyme was also performed. The reactions were incubated at 37° C. and shaken at 200 rpm. The hydrolysis of chlorogenic acid to caffeic acid was monitored by HPLC analysis t=3 hr.

| Control Reaction | | Viscozyme Reaction | |
|---|---|---|---|
| Chlorogenic acid (mg/ml) | Caffeic acid (mg/ml) | Chlorogenic acid (mg/ml) | Caffeic acid (mg/ml) |
| 1.04 | 0 | 0 | 0.65 |

EXAMPLE 8
Ability of Celluzyme to release sinapic acid from rape meal

Method

Rape meal (4 g) was added to water (40 ml, pH 7.0) containing Celluzyme (80 mg; Novo Nordisk) in a water jacketed reaction cell (45° C.) and stirred using a magnetic follower. A pH stat was used to hold the reaction at pH 7.0 by dosing aqueous sodium hydroxide (1.0 M). After 28.25 hr the amount of sinapic acid extracted was measured by HPLC.

Yield of sinapic acid=0.757% w/w rape meal.

Yield of sinapic acid=69% of total sodium hydroxide extractable sinapic acid.

A control reaction (4 g rape meal in 40 ml water) without addition of Celluzyme was performed. After 28.25 hr the amount of sinapic acid extracted was measured by HPLC.

Yield of sinapic acid=0.184% w/w rape meal.

Yield of sinapic acid=17% of total sodium hydroxide extractable sinapic acid.

The total sinapic acid content of rape meal was determined by incubating rape meal (500 mg) in aqueous sodium hydroxide (1.0 M, 10 ml) overnight at 30° C. and 200 rpm. The reaction mixture was neutralised with aqueous hydrochloric acid (1.0 M) and the amount of sinapic acid measured by HPLC.

Yield=1.1% w/w rape meal.

HPLC conditions: $C_{18}$ reverse phase column, 2 ml/min flow rate, 290 nm detector absorbance, acetonitrile/water (20:80)+1% acetic acid mobile phase. Sinapic acid retention time was comparable to standards for both the enzymatic and control reactions.

EXAMPLE 9
Nitrogen analysis of sunflower meal: untreated and Celluzyme+extraction treated Method Sample 1: Untreated sunflower meal was ground into a fine powder using a mortar and pestle (sample mass 607 mg).

Sample 2: Sunflower meal treated with Celluzyme at pH 5.0. Treated meal (2.72 g) was repeatedly extracted with ethyl acetate (1×2.8 ml+6×2.0 ml). The extracted meal was dried for 1.5 hr at 50° C., ground to a powder as described for Sample 1 and dried overnight at 50° C. (sample mass 441 mg).

Sample 3: Sunflower meal treated with Celluzyme at pH 7.0 (protein extract removed). Sunflower meal treated with Celluzyme and extracted with ethyl acetate in a similar manner as described in Example 1 (proteinaceous layer formed on extraction was not added back to the meal). The extracted meal was dried for 0.5 hr at 50° C., ground to a powder as described for Sample 1 and further dried for 2 hr at 50° C. (sample mass 713 mg).

Sample 4: Sunflower meal treated with Celluzyme at pH 7.0 (protein extract not removed).

Sunflower meal treated with Celluzyme as described in Example 1 was extracted with ethyl acetate (6 extractions, total vol. 21.9 ml; proteinaceous layer formed on extraction was added back to the meal). The extracted meal was dried for 0.5 hr at 100° C., ground to a powder as described for Sample 1 and further dried for 2 hr at 50° C. (sample mass 171 mg).

Nitrogen analysis:

Samples 1–4 were analysed for Nitrogen using a Fisons NA2000 analyser (combustion at 1800° C. followed by quantification on for nitrogen gas by gas chromatographic analysis).

| Sample No. | | Nitrogen (%) | Protein (%) | Mean Protein (%) |
|---|---|---|---|---|
| 1 | Untreated | 4.54 | 28.39 | 28.36 |
| | | 4.53 | 28.32 | |
| 2 | Treated pH5.0 | 4.15 | 25.92 | 25.92 |
| | (plus protein) | 4.15 | 25.92 | |
| 3 | Treated pH7.0 | 4.02 | 25.12 | 25.2 |
| | (minus protein) | 4.04 | 25.27 | |
| 4 | Treated pH7.0 | 4.53 | 28.34 | 28.28 |
| | (plus protein) | 4.51 | 28.22 | |

Results demonstrate that removal of the proteinaceous layer formed on ethyl acetate extraction of the meal reduces the estimated protein content of the meal by 3% (samples 3 and 4). If the protein layer is retained with the extracted meal the estimated protein content remains the same as untreated meal (samples 1 and 4). Extraction of the meal at pH 5.0 leads to a reduction in protein content compare to untreated and pH 7 extracted meal samples.

EXAMPLE 10

Enzyme selection protocol

Enzyme preparations were tested by adding the enzyme to a 2 mg/ml solution of chlorogenic acid in deionised water, the reaction mixture being stirred and heated to 45° C. at both pH 7.0 and 5.0 for separate reactions. The reaction was followed on a pH-stat by back titration with 0.01 M sodium hydroxide solution and the rate and extent of uptake of base was observed.

Enzymes showing significant hydrolysis of the substrate were then assayed for the production of caffeic acid by HPLC to confirm the desired activity. Preparations which displayed the required hydrolysis were tested further.

Enzyme preparations from the first conversion, above, were then tested for substantial protease activity as follows. A standard 2 mg/ml solution of bovine serum albumin in pH 7.5, 0.5 M phosphate buffer was treated with enzyme preparation and the resulting mixture stirred at 45° C. for 3 hours. The solution was assayed for soluble protein using standard methods such as the Bradford Assay [method of M. M. Bradford, Anal. Biochem, 1974, 72, 248–254] or a commercial protein assay kit such as that provided by Biorad Laboratories. No substantial protease activity of a test enzyme is indicated when there is no greater loss of measured protein than control reactions which do not contain the test enzyme.

Enzymes which displayed ester hydrolytic activity against chlorogenic acid but no significant hydrolytic activity against bovine serum albumin were regarded as positive in this screen and further tested for hydrolysis of chlorogenic acid in plant meal and non hydrolysis of protein in plant meal. Enzymes displaying these activities are preferred enzymes for use in the methods of the invention.

EXAMPLE 11

Alternative methods for the removal of the caffeic acid from the sunflower meal reaction mixture Method Sunflower meal was treated with Celluzyme as described in Example 1 but instead of acidification with concentrated hydrochloric acid and extraction using ethyl acetate the following procedures were employed:

i) Separation of the aqueous phase from the meal followed by ethyl acetate extraction. A sample of sunflower meal (approx. 412 g) treated with Celluzyme to hydrolyse chlorogenic acid to caffeic acid was pressed using a Walker Desmond Vigo wine press to separate the aqueous phase (980 ml) from the damp sunflower meal (512 g). The aqueous phase was then acidified to pH 3 with concentrated hydrochloric acid and extracted with ethyl acetate (1000 ml+500 ml), the phases separated, pooled, and the organic phase dried over sodium sulphate and dried with heating in vacuo.

Yield of extract=1.95 g (caffeic acid content 54% w/w).

Yield of treated sunflower meal (over dried)=283 g

Optionally the precipitate formed upon acidification of the aqueous phase was removed prior to extraction (see next example).

ii) Separation of the aqueous phase from the meal followed by evaporation.

A sample of Celluzyme treated sunflower meal was pressed as described in (i). The aqueous phase was then dried with heating in vacuo.

Yield of extract=115 g (caffeic acid contact 0.93% w/w).

Yield of treated sunflower meal (over dried)=288 g.

EXAMPLE 12

Isolation of protein from sunflower meal treated with Celluzyme

Method

Sunflower meal was treated as described in Example 1 (total mass 412 g) using Celluzyme but instead of terminating the reaction by addition of hydrochloric acid the following procedure was adopted. The reaction mixture was pressed using a Walker Desmond Vigo wine press to separate the solid meal from the aqueous phase containing soluble protein and caffeic acid. The aqueous phase was adjusted to pH 5.0 and then pH 3.0 using concentrated hydrochloric acid. The precipitate formed on each pH adjustment was collected by centrifugation and air dried. The protein content of the dried precipitate was determined by the difference between the protein remaining in the aqueous phase before and after pH adjustment. The protein concentration was determined using the Biorad protein assay and comparing to a standard curve to protein concentrations. The caffeic acid can be recovered from the aqueous phase by organic extraction as described in the previous example.

|       | Mass of dried precipitate (g) | Protein concentration (% w/w) |
|-------|-------------------------------|-------------------------------|
| pH5.0 | 19.01                         | 91                            |
| pH3.0 | 15.44                         | 5                             |

EXAMPLE 13

Extraction of caffeic acid from sunflower meal treated with Celluzyme

Method

Sunflower meal (825 g) was treated with Celluzyme as described in Example 1 but n-butan-1-ol (2500 ml+1000 ml) was substituted in place of the ethyl acetate. The n-butan-1-ol was separated from the aqueous phase, dried over sodium sulphate and dried with heating in vacuo.

Yield of extract=26.29 g (caffeic acid content 16.6% w/w).

Yield of treated sunflower meal (over dried)=541 g.

Yield of treated sunflower mean+aqueous phase (over dried)=656 g

EXAMPLE 14

Enzymatic production of ferulic acid from wheat bran and destarched wheat bran

Method

Wheat bran (500 g) was added to water (10 ml, pH 7.0) containing Celluzyme (10 mg; Novo Nordisk) in a water jacketed reaction cell (45° C.) and stirred using a magnetic follower. A pH stat was used to hold the reaction at pH 7.0 by dosing aqueous sodium hydroxide (0.1 M). After 4 hr the amount of ferulic acid extracted was measured by HPLC.

Yield of ferulic acid=0.05% w/w wheat bran.

Yield of ferulic acid=7% of total sodium hydroxide extractable ferulic acid.

An identical reaction using destarched wheat bran in place of wheat bran was performed. After 4 hr the amount of ferulic acid extracted was again measured by HPLC. Wheat bran was destarched as described by K. G. Johnson et al., Enzyme Microb. Technol. 1988, 10, 403–409. The destarching methods disclosed are generally applicable to all plant materials and can be used to prepare partially or preferably wholly destarched plant material according to a preferred embodiment of the invention.

Yield of ferulic acid=0.5% w/w wheat bran.

Yield of ferulic acid=58% of total sodium hydroxide extractable ferulic acid.

The total ferulic acid content of the wheat bran and destarched wheat bran were determined as described in example 8 for sinapic acid in rape meal.

Yield=0.71% w/w wheat bran.

Yield=0.86% w/w destarched wheat bran.

HPLC conditions: $C_{18}$ reverse phase column, 2 ml/min flow rate, 290 nm detector absorbance, acetonitrile/water (20:80)+1% acetic acid mobile phase.

Ferulic acid retention time was comparable to standards for both the enzymatic and control reactions.

EXAMPLE 15

Enzymatic production of ferulic acid from wheat bran

Method

Wheat bran (500 mg) was added to phosphate buffer (10 ml, 100 mM., pH 7.0) in a universal bottle. Celluzyme (4 mg; Novo Nordisk) and Pulpzyme HC® (100 µl; Novo Nordisk) were added and the reaction incubated at 45° C. and 200 rpm. After 1 hr the amount of ferulic acid extracted was measured by HPLC.

Yield=0.26% w/w wheat bran.

Yield=37% of total sodium hydroxide extractable ferulic acid.

Pulpzyme HC® is a xylanase preparation produced by submerged fermentation of a Bacillus strain. It catalyses the hydrolysis of deacylated xylan substrates. It contains endo-1,4-beta-D-xylanase activity (E.C. 3.2.1.8) and is virtually free of cellulase activity.

The commercial product is available from Novo Nordisk at an activity of 500 EXU/g with one xylanase unit (EXU) being defined as the amount of enzyme which, in standard conditions (pH 9.0, 50° C. (122° F.), 30 minutes incubation), releases a defined amount of dye from dyed RBB xylan. (Details of the analysis method (AF 293.9/1) are available from Novo Nordisk on request)

Pulpzyme HC® is sold for use in the bleach boosting of kraft pulp. It is classified as a xylanase, CAS No. 9025-57-4, and the xylanase is classified in IUB (International Union of Biochemistry) with EC No. 3.2.1.8.

An identical control reaction without addition of Pulpzyme HC was performed. After 1 hr the amount of ferulic acid extracted was again measured by HPLC.

Yield=0.04% w/w wheat bran.

Yield=5% of total sodium hydroxide extractable ferulic acid

The total ferulic acid content of the wheat bran was determined as described in example 8 for sinapic acid in rape meal.

Yield=0.71% w/w wheat bran.

HPLC conditions: $C_{18}$ reverse phase column, 2 ml/min flow rate, 290 nm detector absorbance, acetonitrile/water (20:80)+1% acetic acid mobile phase. Ferulic acid retention time was comparable to standards for both the enzymatic and control reactions.

What is claimed is:

1. A method of treating plant material to improve its nutritional value comprising:

exposing the plant material to a hydrolytic enzyme isolated from Humicola species, which enzyme does not exhibit a substantial proteolytic activity, in an aqueous environment; and removing one or more phenolic compounds produced.

2. A method of preparing a phenolic compound from a plant material comprising;

treating a plant material by exposing it to a hydrolytic enzyme isolated from Humicola species, which enzyme does not exhibit a substantial proteolytic activity, in an aqueous environment; and removing the phenolic compound.

3. A method as claimed in claim 1 or 2, wherein the enzyme is isolated from *Humicola insolens*.

4. A method as claimed in claim 1 or 2, wherein the enzyme is selected from a cellulolytic enzyme preparation produced by submerged fermentation of *Humicola insolens,* a carbohydrase preparation produced by submerged fermentation of *Humicola insolens,* and an enzyme isolated from Humicola species having substantially the same enzymatic activity as the cellulolytic enzyme preparation and the carbohydrase preparation.

5. A method as claimed in claim 4, wherein the enzyme is selected from a cellulolytic enzyme preparation produced by submerged fermentation of *Humicola insolens* and a carbohydrase preparation produced by submerged fermentation of *Humicola insolens.*

6. A method as claimed in claim 1 or 2, wherein the phenolic compound is selected from caffeic acid, ferulic acid, sinapinic acid and coumaric acid.

7. A method as claimed in claim 1 or 2, wherein the enzyme hydrolyses chlorogenic acid to caffeic acid and quinic acid.

8. A method as claimed in claim 1 or 2, the plant material comprising protein, wherein the protein in the treated plant material is precipitated and removed.

9. A feed product comprising treated plant material obtainable by the method of claim 1 or 2.

10. A method as claimed in claim 1 further comprising:
feeding the treated plant material to a human or animal.

11. A method of producing ferulic acid from a plant material comprising treating plant material with a hydrolytic enzyme in an aqueous environment as claimed in claim 1 and removing the ferulic acid product of hydrolysis.

12. A method as claimed in claim 1 or 2, wherein the plant material is from one or more of sunflower, rice, coffee, rape, grape, sugar beet and cereal grains such as wheat and corn.

13. A method as claimed in claim 12, wherein the plant material is from cereal grain.

14. A method as claimed in claim 13, wherein the cereal grain is wheat.

15. A method as claimed in claim 15, wherein the plant material is wheat germ.

16. A method as claimed in claim 15 wherein the plant material is wheat bran.

17. A method of making caffeic acid and quinic acid from a plant material comprising:
treating plant material containing chlorogenic acid with a hydrolytic enzyme isolated from *Humicola* species in an aqueous environment as claimed in claim 1; and
removing the caffeic acid and quinic acid hydrolysis products.

18. A method as claimed in claim 17, wherein the plant material is from sunflower.

19. A method as claimed in any one of claims 2, 11, and 17, wherein the hydrolysis products are removed by solvent extraction.

20. A method as claimed in claim 1 or 2, wherein the weight/volume ratio (w/v) of plant material to water is 1:10 or less dilute.

21. A method as claimed in claim 20, wherein the ratio is 1:5 or less dilute.

22. A method as claimed in claim 21, wherein the ratio is 1:2.

23. A method as claimed in claim 1 or 2, wherein the plant material is wholly, or at least partially destarched.

24. A process for manufacturing a food produce containing treated plant material for administration to a human or animal, the process comprising:
producing treated plant material by the method of claim 1 or claim 2.

* * * * *